US008609903B2

(12) United States Patent
Klaus et al.

(10) Patent No.: US 8,609,903 B2
(45) Date of Patent: Dec. 17, 2013

(54) PROCESS FOR PREPARING HYDROXY-SUBSTITUTED AROMATIC ALDEHYDES

(75) Inventors: Ebel Klaus, Lampertheim (DE); Stefan Rüdenauer, Worms (DE)

(73) Assignee: BASF SE (DE)

( * ) Notice: Subject to any disclaimer, the term of this patent is extended or adjusted under 35 U.S.C. 154(b) by 130 days.

(21) Appl. No.: 13/078,195

(22) Filed: Apr. 1, 2011

(65) Prior Publication Data
US 2011/0245544 A1 Oct. 6, 2011

Related U.S. Application Data

(60) Provisional application No. 61/319,878, filed on Apr. 1, 2010.

(51) Int. Cl.
C07C 45/90 (2006.01)
(52) U.S. Cl.
USPC .......................................... 568/433; 568/432
(58) Field of Classification Search
None
See application file for complete search history.

(56) References Cited

U.S. PATENT DOCUMENTS

| 2,100,228 | A | * | 11/1937 | Tinker et al. ............... 568/763 |
| 2011/0118510 | A1 | | 5/2011 | Weis et al. |
| 2011/0196176 | A1 | | 8/2011 | Lanver et al. |

FOREIGN PATENT DOCUMENTS

| JP | 63044546 A | * | 2/1988 |
| WO | WO-2010/012675 A1 | | 2/2010 |
| WO | WO-2011/048012 A1 | | 4/2011 |
| WO | WO-2011/048068 A2 | | 4/2011 |
| WO | WO-2011/067386 A2 | | 6/2011 |

OTHER PUBLICATIONS

International Search Report for PCT/EP2011/054851, dated Jun. 7, 2011.
Bao, K., et al., "Selective demethylation and debenzylation of aryl ethers by magnesium iodide under solvent-free conditions and its application to the total synthesis of natural products," Org. Biomol. Chem., (2007), vol. 7, pp. 5084-5090.
Bhattacharya, A., et al., "Surfactant-mediated solvent-free dealkylative cleavage of ethers and esters and trans-alkylation under neutral conditions," Tetrahedron Letters, (2006), vol. 47, pp. 565-567.
Demyttenaere, J., et al., "Synthesis of 6-methoxy-4H-1-benzopyran-7-ol, a character donating component of the fragrance of *Wisteria sinensis*," Tetrahedron, (2002), vol. 58, pp. 2163-2166.
Fang, Z., et al., "Lithium chloride-catalyzed selective demethylation of aryl methyl ethers under microwave irradiation," Journal of Molecular Catalysis A: Chemical, (2007), vol. 274, pp. 16-23.
Pearl, I.A., et al., "Reactions of Vanillin and its Derived Compounds. XVII. A Synthesis of Syringaldehyde from Vanillin," J. Am. Chem. Soc., (1952), vol. 74, pp. 4262-4263.
Prager, R.H., et al., "Selective Demethylation of 3,4-Dimethoxybenzaldehyde," Tetrahedron Letters, (1967), vol. 38, pp. 3661-3664.
Ren, X., et al., "First enantioselective synthesis of daphneticin and its regioisomer," Tetrahedron: Asymmetry, (2002), vol. 13, pp. 1799-1804.

* cited by examiner

*Primary Examiner* — Sudhakar Katakam
(74) *Attorney, Agent, or Firm* — Novak Druce Connolly Bove + Quigg LLP

(57) ABSTRACT

The present invention therefore relates to a process for preparing an aldehyde of the formula (I)

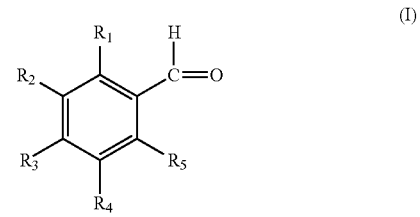

where one, two or all three radicals from the group of $R_1$, $R_3$ and $R_5$ are hydroxyl, and that radical or those radicals from the group of $R_1$, $R_3$ and $R_5$ which are not hydroxyl are each independently hydrogen, $C_1$-$C_8$-alkyl or $C_6$-$C_{14}$-aryl, and $R_2$ and $R_4$ are each independently hydrogen, $C_1$-$C_8$-alkyl, $C_1$-$C_8$-alkoxy or $C_6$-$C_{14}$-aryl, which comprises converting an aldehyde of the formula (II)

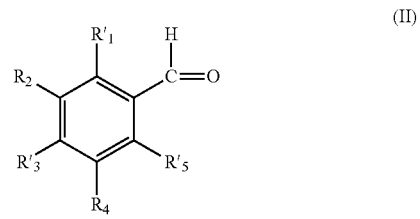

in which one, two or all three radicals from the group of $R'_1$, $R'_3$ and $R'_5$ are $C_1$-$C_8$-alkoxy, and that radical or those radicals from the group of $R'_1$, $R'_3$ and $R'_5$ which are not $C_1$-$C_8$-alkoxy are each independently hydrogen, $C_1$-$C_8$-alkyl or $C_6$-$C_{14}$-aryl, and $R_2$ and $R_4$ are each as defined for formula (I), at elevated temperature and elevated pressure in the presence of $(C_1$-$C_4$-alkyl$)_2$-amine, and then isolating the reaction product of the formula (I).

22 Claims, No Drawings

PROCESS FOR PREPARING HYDROXY-SUBSTITUTED AROMATIC ALDEHYDES

CROSS-REFERENCE TO RELATED APPLICATIONS

This application claims benefit (under 35 USC 119(e)) of U.S. Provisional Application 61/319,878, filed Apr. 1, 2010.

BACKGROUND OF THE INVENTION

The invention provides a process for preparing aromatic aldehydes which possess at least one hydroxyl group on the aromatic ring.

One example of a literature procedure for preparation of hydroxy-substituted aromatic aldehydes is the O-demethylation of aromatic methyl ethers. However, the industrial scale use of known methods for O-demethylation is limited since, for example, the reagents used are expensive, promote corrosion and/or require very severe reaction conditions, for example reaction by means of sodium thioethoxide at 150° C. in dimethylformamide or reaction with sodium in liquid ammonia. Reactions with highly reactive reagents, for example boron tribromide, aluminum trichloride or boron trichloride, do lead to a rapid conversion but exhibit a significantly reduced selectivity as soon as two or three aromatic methoxy groups are present on the aromatic ring. The use of strong Lewis acids or Lewis bases also becomes difficult when the aromatic comprises further functional groups, for example aldehyde, keto or benzylic alcohol groups, since side reactions can occur more frequently in this arrangement.

The regioselective O-demethylation of poly-methoxy-substituted benzaldehydes is known from the literature, for example:

Demyttenaere et al., Tetrahedron 2002, 58, 2163-2166, uses $AlCl_3$ for demethylation of 2,3,4-trimethoxybenzaldehyde. The demethylation is effected in the presence of a large excess of $AlCl_3$ in the ortho and para positions.

Ren et al., Tetrahedron Asymm. 2002, 13, 1799-1804, uses a piperidine-water mixture for demethylation of 2,3,4-trimethoxybenzaldehyde. Disadvantages are the long reaction times and the slightly reduced applicability of this reaction to only highly electron-rich compounds.

Bhattacharya et al., Tetrahedron Lett. 2006, 565-567, uses NaSCN and Triton-X 405 for demethylation of 3,4-dimethoxybenzaldehyde. This conversion requires relatively high temperatures.

Fang et al., J. Mol. Cat. A: Chemical 2007, 16-23, uses LiCl in dimethylformamide under microwave irradiation for demethylation of 2,3,4-trimethoxybenzaldehyde and 3,4-dimethoxybenzaldehyde. The conversion is performed in the presence of expensive LiCl. The conversion also forms toxic methyl chloride.

Prager and Tan, *Tetrahedron Lett.* 1967, 38, 3661-3664, use Lewis acids, for example $AlCl_3$, for demethylation of 3,4-dimethoxybenzaldehyde. A disadvantage in this procedure is the corrosion problems with this reagent, and the requirement for exact setting of the molar ratio.

Pearl et al., J. Am. Chem. Soc. 1952, 74, 4262-4263, uses sulfuric acid for demethylation of 2,3,4-trimethoxybenzaldehyde. Disadvantages are the corrosion problems with this reagent, and, when this procedure is applied to 3,4-dimethoxybenzaldehyde, a conversion in reverse regioselectivity compared to 2,3,4-trimethoxybenzaldehyde.

BRIEF SUMMARY OF THE INVENTION

Proceeding from this prior art, it was an object of the present invention to provide a process for preparing a hydroxy-substituted aromatic aldehyde, which can be performed in a manner which is easy to manage in terms of process technology and with a high overall yield with maximum regioselectivity on the industrial scale. It should be possible to utilize inexpensive starting compounds and reagents which are easy to recover and have good reusability.

It has been found that, surprisingly, the reaction of alkoxybenzaldehydes with dialkylamine at elevated temperature and elevated pressure leads to a rapid and also regioselective O-dealkylation.

The present invention therefore provides a process for preparing an aldehyde of the formula (I)

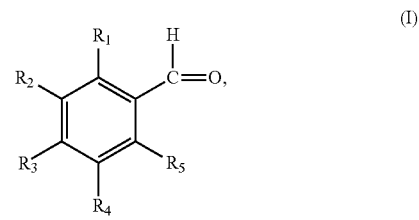

where one, two or all three radicals from the group of $R_1$, $R_3$ and $R_5$ are hydroxyl, and that radical or those radicals from the group of $R_1$, $R_3$ and $R_5$ which are not hydroxyl are each independently hydrogen, $C_1$-$C_8$-alkyl or $C_6$-$C_{14}$-aryl, and $R_2$ and $R_4$ are each independently hydrogen, $C_1$-$C_8$-alkyl, $C_1$-$C_8$-alkoxy or $C_6$-$C_{14}$-aryl, which comprises converting an aldehyde of the formula (II)

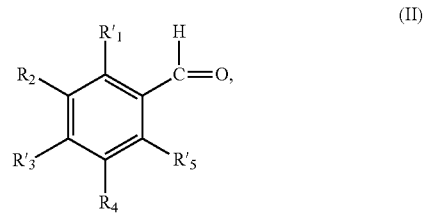

in which one, two or all three radicals from the group of $R'_1$, $R'_3$ and $R'_5$ are $C_1$-$C_8$-alkoxy, and that radical or those radicals from the group of $R'_1$, $R'_3$ and $R'_5$ which are not $C_1$-$C_8$-alkoxy are each independently hydrogen, $C_1$-$C_8$-alkyl or $C_6$-$C_{14}$-aryl, and $R_2$ and $R_4$ are each as defined for formula (I), at elevated temperature and elevated pressure in the presence of $(C_1$-$C_4$-alkyl$)_2$-amine, and then isolating the reaction product of the formula (I).

DETAILED DESCRIPTION OF THE INVENTION

The process according to the invention is notable for a surprisingly high regioselectivity. For example, by the process according to the invention, a 3,4,5-trimethoxybenzaldehyde is converted very selectively to the 4-hydroxy-3,5-dimethoxybenzaldehyde.

Examples of useful radicals for the $R_1$, $R_2$, $R_3$, $R_4$, $R_5$, $R'_1$, $R'_3$ and $R'_5$ radicals as $C_1$-$C_8$-alkyl include: methyl, ethyl, n-propyl, isopropyl, n-butyl, sec-butyl, tert-butyl, isobutyl, n-pentyl, n-hexyl or n-octyl, where the $C_1$-$C_8$-alkyl radicals mentioned may be substituted, for example, by halogen, such as chlorine, fluorine or bromine, or hydroxyl. Preference is given to $C_1$-$C_4$-alkyl radicals and particular preference to $C_1$-$C_3$-alkyl radicals. Very particularly preferred alkyl radicals are methyl and ethyl.

Preferred useful radicals for the $R_1$, $R_2$, $R_3$, $R_4$, $R_5$, $R'_1$, $R'_3$ and $R'_5$ radicals as $C_6$-$C_{14}$-aryl are the phenyl or naphthyl radical, which radicals may be further substituted on the aromatic system, for example by halogen, for example fluorine, chlorine or bromine, $C_1$-$C_4$-alkyl, for example methyl, ethyl, n-propyl, isopropyl, n-butyl, sec-butyl, tert-butyl and isobutyl, $C_1$-$C_4$-alkoxy, for example methoxy, ethoxy, n-propoxy, isopropoxy, n-butoxy and tert-butoxy.

Examples of useful radicals for the $R_2$, $R_4$, $R'_1$, $R'_3$ and $R'_5$ radicals as $C_1$-$C_8$-alkoxy include: methoxy, ethoxy, n-propoxy, isopropoxy, n-butoxy, tert-butoxy, n-pentyloxy and n-octyloxy. Preference is given to $C_1$-$C_4$-alkoxy radicals, and particularly preferred radicals are methoxy and ethoxy. For the $R'_1$, $R'_3$ and $R'_5$ radicals, the methoxy radical is very particularly preferred. For the $R_2$ and $R_4$ radicals, very particularly preferred $C_1$-$C_4$-alkoxy radicals are methoxy and ethoxy.

The inventive conversion is effected preferably at a temperature in the range between 40 and 300° C., more preferably in the range between 60 and 250° C., and most preferably in the range between 80 and 160° C.

The process according to the invention is performed under a pressure between 1 and 100 bar, preference being given to a pressure between 2 and 60 bar. Very particular preference is given to a pressure between 2 and 20 bar.

The reaction can be performed over a prolonged period, the reaction time of the conversion being in the range between 1 and 48 hours. Preference is given to a reaction time between 2 and 18 hours, and the reaction time is most preferably between 6 and 15 hours.

The process according to the invention is performed in the presence of $(C_1$-$C_4$-alkyl$)_2$ amine. Especially useful dialkylamines include: dimethylamine, diethylamine, di-n-propylamine, diisopropylamine. The amines are more preferably dimethylamine and diethylamine. Very particular preference is given to dimethylamine.

In a likewise preferred configuration of the process according to the invention, the conversion is effected in the presence of the dialkylamine in aqueous solution. Dimethylamine has very good water solubility. It is thus possible to use commercial aqueous solutions of dimethylamine in water. Commercial solutions of dimethylamine in water comprise approx. 35 to 65 mol % dimethylamine. Diethylamine is liquid and can likewise be used as an aqueous solution. Di-n-propylamine and diisopropylamine can likewise be used as an aqueous solution. In a preferred embodiment of the process according to the invention, dimethylamine is used in aqueous solution. The dimethylamine content of the aqueous solution is preferably 40 to 60 mol %.

In a further embodiment, the process according to the invention can be performed in the presence of one or more further solvents. Useful further solvents include, in particular, polar solvents, for example acetonitrile, acetone, ethyl acetate, or else alcohols, for example methanol, ethanol.

In a further preferred embodiment of the process according to the invention, an aldehyde of the formula (II) in which one, two or all three radicals from the group of $R'_1$, $R'_3$ and $R'_5$ are $C_1$-$C_4$-alkoxy, especially methoxy, and that radical or those radicals from the group of $R'_1$, $R'_3$ and $R'_5$ which are not $C_1$-$C_4$-alkoxy, especially methoxy, are each independently hydrogen, $C_1$-$C_4$-alkyl or $C_6$-$C_{10}$-aryl, and $R_2$ and $R_4$ are each independently hydrogen, $C_1$-$C_8$-alkyl, $C_1$-$C_8$-alkoxy or $C_6$-$C_{14}$-aryl, is used.

In a particularly preferred embodiment of the process according to the invention, an aldehyde of the formula (II) in which one, two or all three radicals from the group of $R'_1$, $R'_3$ and $R'_5$ are methoxy, and that radical or those radicals from the group of $R'_1$, $R'_3$ and $R'_5$ which are not methoxy are each independently hydrogen, $C_1$-$C_4$-alkyl or $C_6$-$C_{10}$-aryl, and $R_2$ and $R_4$ are each hydrogen, $C_1$-$C_4$-alkyl, $C_1$-$C_4$-alkoxy or $C_6$-$C_{10}$-aryl, is used.

In a very particularly preferred embodiment of the process according to the invention, an aldehyde of the formula (IIa)

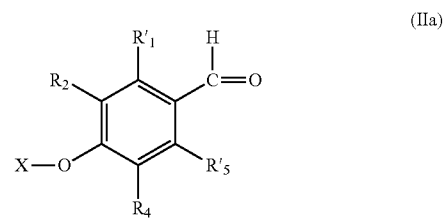

in which $R'_1$ and $R'_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl, and X is $C_1$-$C_4$-alkyl, especially methyl, is converted to an aldehyde of the formula (Ia)

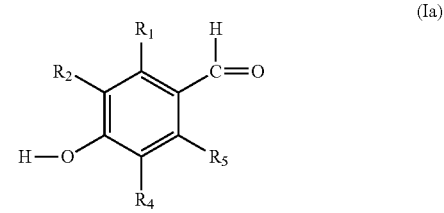

in which $R_1$ and $R_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl.

In a likewise very particularly preferred embodiment of the process according to the invention, an aldehyde of the formula (IIb)

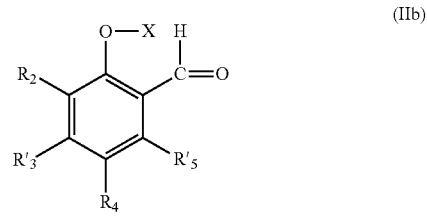

in which $R'_3$ and $R'_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl, and X is $C_1$-$C_4$-alkyl, especially methyl, is converted to an aldehyde of the formula (Ib)

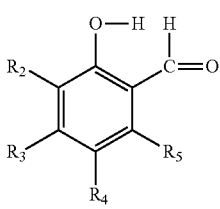

in which $R_3$ and $R_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl.

In an even more preferred embodiment of the process according to the invention, an aldehyde of the formula (IIa) in which $R'_1$, $R'_5$, $R_2$ and $R_4$ are each hydrogen, and X is $C_1$-$C_4$-alkyl, especially methyl, is converted to an aldehyde of the formula (Ia) in which $R_1$, $R_2$, $R_4$ and $R_5$ are each hydrogen.

In a further even more preferred embodiment of the process according to the invention, an aldehyde of the formula (IIa) in which $R'_1$, $R'_5$ and $R_4$ are each hydrogen and $R_2$ is $C_1$-$C_4$-alkoxy, especially methoxy, and X is $C_1$-$C_4$-alkyl, especially methyl, is converted to an aldehyde of the formula (Ia) in which $R^1$, $R^4$ and $R^5$ are each hydrogen and $R_2$ is $C_1$-$C_4$-alkoxy, especially methoxy.

In a likewise even more preferred embodiment of the process according to the invention, an aldehyde of the formula (IIa) in which $R'_1$ and $R'_5$ are each hydrogen and $R_2$ and $R_4$ are each $C_1$-$C_4$-alkoxy, especially methoxy, and X is methyl, is converted to an aldehyde of the formula (Ia) in which $R_1$ and $R_5$ are each hydrogen and $R_2$ and $R_4$ are each $C_1$-$C_4$-alkoxy, especially methoxy.

In a further even more preferred embodiment of the process according to the invention, an aldehyde of the formula (IIc).

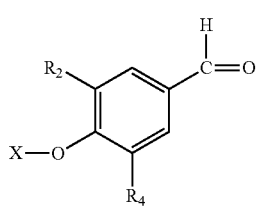

in which $R_2$ and $R_4$ are each independently hydrogen or $C_1$-$C_4$-alkoxy, preferably hydrogen, methoxy or ethoxy, and X is $C_1$-$C_4$-alkyl, preferably methyl, is converted to an aldehyde of the formula (Ic)

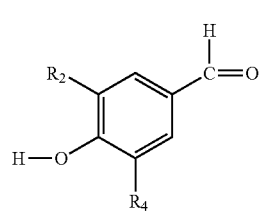

in which $R_2$ and $R_4$ are each as defined for formula (IIc). The conversion is effected preferably in the presence of dimethylamine at a temperature in the range between 130 and 150° C. and a pressure of 5 to 15 bar. After a reaction time of 12 to 15 hours, the conversion has ended.

Useful starting compounds for the process according to the invention include, for example, the following compounds of the formula (II): 2-methoxybenzaldehyde, 4-methoxybenzaldehyde, 2-ethoxybenzaldehyde, 4-ethoxybenzaldehyde, 3,4-dimethoxybenzaldehyde, 3,4-diethoxybenzaldehyde, 3,4,5-trimethoxybenzaldehyde, 3-methyl-4-methoxybenzaldehyde, 3-ethyl-4-methoxybenzaldehyde, 2-methyl-5-methoxybenzaldehyde, 2,5-dimethyl-4-methoxybenzaldehyde, 2-phenyl-4-ethoxybenzaldehyde.

The inventive conversion is effected under pressure, and so pressure-resistant apparatus has to be used. Useful pressure-resistant apparatus includes commercial autoclaves or else continuous pressure-resistant apparatus, for example tubular reactors.

Autoclaves must be able to withstand relatively high pressures. Typical laboratory autoclaves withstand approx. 150 bar. The outer walls are thick and often consist of stainless steels in order to prevent corrosion and not to contaminate the charge. For the performance of reactions with aggressive chemicals, autoclaves with internal Teflon coatings are obtainable. Specific designs allow pressures up to 7000 bar and temperatures above 600° C. In the laboratory, autoclaves with a volume of a few milliliters up to several liters are widespread, which typically possess a manometer, a thermometer and a gas valve.

The reaction products obtained by the process according to the invention are recovered by working up the reaction mixture by customary processes, for example extraction, distillation and/or crystallization. For example, excess dimethylamine and water are removed under reduced pressure. Subsequently, a water-immiscible solvent is added, for example diethyl ether, methyl tert-butyl ether or the like, the mixture is acidified with an acid, for example 30% HCl in water, and, after the phase separation and after removal of all volatile constituents of the organic phase, the product can be obtained in good yield, optionally after distillation or crystallization.

The conversion to be performed in accordance with the invention can be performed either batchwise or continuously. For example, in the batchwise case, the conversion can be undertaken in such a way that the aldehyde of the formula (II) and, for example, an aqueous solution of the dialkylamine, optionally in the presence of a further solvent, for example methanol, are initially charged in a suitable reaction vessel, for example an autoclave, and the conversion is undertaken at elevated temperature and under elevated pressure. On completion of the reaction, as described above, excess dialkylamine and water are removed under reduced pressure, a water-insoluble solvent, for example methyl tert-butyl ether, is added, the mixture is acidified with, for example, 30% HCl in water, and, after phase separation and removal of all volatile constituents of the organic phase, the reaction product of the formula (I) is isolated from the reaction mixture obtained, by suitable separating processes. The sequence of contacting of the individual reaction components is not critical and can be varied according to the particular process technology configuration.

In a preferred embodiment, the dealkylation to be performed in accordance with the invention, especially the demethylation, of the aldehyde of the formula (II) in the presence of the dialkylamine is performed continuously, for example in a continuous tubular reactor, at elevated temperature and elevated pressure. For this purpose, it is possible to prepare, for example, a mixture of the starting materials to be converted, the aldehyde of the formula (II) and the dialkylamine, optionally as an aqueous solution, and to bring this mixture continuously into mutual contact. For this purpose, the starting components selected, aldehyde of the formula (II) and dialkylamine, can be introduced into a tubular reactor and the starting materials can be introduced continuously into it, and the reaction mixture can be discharged continuously.

The invention is illustrated in detail by the examples which follow without restricting it thereto. In the examples, all figures in % are % by weight.

EXAMPLE 1

A 100 ml glass autoclave is charged with 8.84 g (65.0 mmol) of 4-methoxybenzaldehyde and 51.2 g (455 mmol) of dimethylamine (40% solution in water). The autoclave is closed and the biphasic reaction mixture is stirred at 140° C. (autogenous pressure 7.5 bar) for 15 h. Excess dimethylamine and water are removed under reduced pressure, methyl tert-butyl ether is added and the mixture is acidified with 30% hydrochloric acid in water. After phase separation and removal of all volatile constituents of the organic phase, 6.5 g (0.53 mmol, 81% yield) of 4-hydroxybenzaldehyde are obtained.

EXAMPLE 2

A metal autoclave is charged with 14.0 g (84.0 mmol) of 3,4-dimethoxybenzaldehyde and 120 g (1.0 mol) of dimethylamine (40% solution in water). The autoclave is closed and the biphasic reaction mixture is stirred at 140° C. (autogenous pressure 14 bar) for 10 h. Excess dimethylamine and water are removed under reduced pressure, methyl tert-butyl ether is added and the mixture is acidified with 30% hydrochloric acid in water. After phase separation and removal of all volatile constituents of the organic phase, 8.5 g (56.0 mmol, 67% yield) of 4-hydroxy-3-methoxybenzaldehyde are obtained.

EXAMPLE 3

A 100 ml glass autoclave is charged with 11.8 g (60.0 mmol) of 3,4,5-trimethoxybenzaldehyde and 47.2 g (420 mmol) of dimethylamine (40% solution in water). The autoclave is closed and the biphasic reaction mixture is stirred at 140° C. (autogenous pressure 10 bar) for 18 h. Excess dimethylamine and water are removed under reduced pressure, methyl tert-butyl ether is added and the mixture is acidified with 30% hydrochloric acid in water. After phase separation and removal of all volatile constituents of the organic phase, 4-hydroxy-3,5-dimethoxybenzaldehyde is obtained in a yield of 72%.

The invention claimed is:

1. A process for preparing an aldehyde of the formula (I)

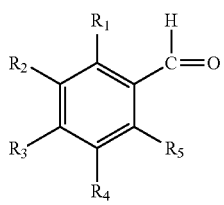

(I)

wherein one, two or all three radicals from the group of $R_1$, $R_3$ and $R_5$ are hydroxyl, and that radical or those radicals from the group of $R_1$, $R_3$ and $R_5$ which are not hydroxyl are each independently hydrogen, $C_1$-$C_8$-alkyl or $C_6$-$C_{14}$-aryl, and $R_2$ and $R_4$ are each independently hydrogen, $C_1$-$C_8$-alkyl, $C_1$-$C_8$-alkoxy or $C_6$-$C_{14}$-aryl, which comprises converting an aldehyde of the formula (II)

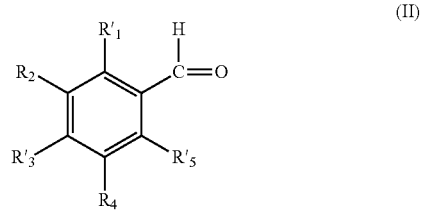

(II)

in which one, two or all three radicals from the group of $R'_1$, $R'_3$ and $R'_5$ are $C_1$-$C_8$-alkoxy, and that radical or those radicals from the group of $R'_1$, $R'_3$ and $R'_5$ which are not $C_1$-$C_8$-alkoxy are each independently hydrogen, $C_1$-$C_8$-alkyl or $C_6$-$C_{14}$-aryl, and $R_2$ and $R_4$ are each as defined for formula (I), at elevated temperature and elevated pressure in the presence of $(C_1$-$C_4$-alkyl$)_2$-amine, and then isolating the reaction product of the formula (I).

2. The process according to claim 1, wherein the conversion is effected at a temperature between 40 and 300° C.

3. The process according to claim 1, wherein the conversion is effected at a temperature between 80 and 160° C.

4. The process according to claim 1, wherein the conversion is effected at a pressure between 1 and 100 bar.

5. The process according to claim 1, wherein the conversion is effected at a pressure between 2 and 20 bar.

6. The process according to claim 1, wherein the reaction time is between 1 and 48 hours.

7. The process according to claim 1, wherein the reaction time is between 6 and 15 hours.

8. The process according to claim 1, wherein the conversion is effected in the presence of dimethylamine or diethylamine.

9. The process according to claim 1, wherein the conversion is effected in the presence of dimethylamine.

10. The process according to claim 1, wherein the conversion is effected in the presence of the $(C_1$-$C_4$-alkyl$)_2$-amine in aqueous solution.

11. The process according to claim 10, wherein the conversion is effected in the presence of dimethylamine in aqueous solution.

12. The process according to claim 1, wherein the aldehyde of the formula (II) in which one, two or all three radicals from the group of $R'_1$, $R'_3$ and $R'_5$ are $C_1$-$C_4$-alkoxy, and that radical or those radicals from the group of $R'_1$, $R'_3$ and $R'_5$ which are not $C_1$-$C_4$-alkoxy, are each independently hydrogen, $C_1$-$C_4$-alkyl or $C_6$-$C_{10}$-aryl, and $R_2$ and $R_4$ are each as defined for formula (I) is used.

13. The process according to claim 1, wherein the aldehyde of the formula (II) in which one, two or all three radicals from the group of $R'_1$, $R'_3$ and $R'_5$ are $C_1$-$C_4$-alkoxy, and that radical or those radicals from the group of $R'_1$, $R'_3$ and $R'_5$ which are not $C_1$-$C_4$-alkoxy, are each independently hydrogen, $C_1$-$C_4$-alkyl or $C_6$-$C_{10}$-aryl, and $R_2$ and $R_4$ are each hydrogen, $C_1$-$C_4$-alkyl, $C_1$-$C_4$-alkoxy or $C_6$-$C_{10}$-aryl, is used.

14. The process according to claim 13, wherein an aldehyde of the formula (IIa)

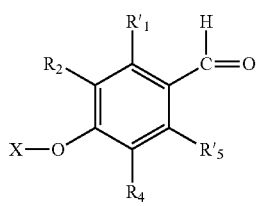

(IIa)

in which $R'_1$ and $R'_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl, and X is $C_1$-$C_4$-alkyl, is converted to an aldehyde of the formula (Ia)

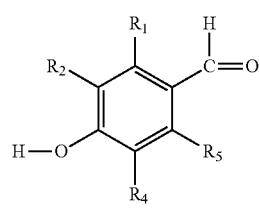

(Ia)

in which $R_1$ and $R_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl.

15. The process according to claim 13, wherein an aldehyde of the formula (IIb),

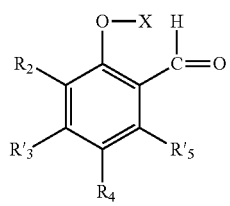

(IIb)

in which $R'_3$ and $R'_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl, and X is $C_1$-$C_4$-alkyl, is converted to an aldehyde of the formula (Ib)

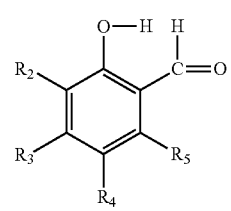

(Ib)

in which $R_3$ and $R_5$ are each independently hydrogen, $C_1$-$C_4$-alkyl or $C_6$-$C_{10}$-aryl, and $R_2$ and $R_4$ are each independently hydrogen, $C_1$-$C_4$-alkyl, $C_1$-$C_4$-alkoxy or $C_6$-$C_{10}$-aryl.

16. The process according to claim 14, wherein the aldehyde of the formula (IIa) in which $R'_1$, $R'_5$, $R_2$ and $R_4$ are each hydrogen, and X is $C_1$-$C_4$-alkyl, is converted to an aldehyde of the formula (Ia) in which $R_1$, $R_2$, $R_4$ and $R_5$ are each hydrogen.

17. The process according to claim 14, wherein an aldehyde of the formula (IIa) in which $R'_1$, $R'_5$ and $R_4$ are each hydrogen and $R_2$ is $C_1$-$C_4$-alkoxy and X is $C_1$-$C_4$-alkyl, is converted to an aldehyde of the formula (Ia) in which $R_1$, $R_4$ and $R_5$ are each hydrogen and $R_2$ is $C_1$-$C_4$-alkoxy.

18. The process according to claim 14, wherein the aldehyde of the formula (IIa) in which $R'_1$ and $R'_5$ are each hydrogen and $R_2$ and $R_4$ are each $C_1$-$C_4$-alkoxy, and X is methyl, is converted to an aldehyde of the formula (Ia) in which $R_1$ and $R_5$ are each hydrogen and $R_2$ and $R_4$ are each $C_1$-$C_4$-alkoxy.

19. The process according to claim 14, wherein the aldehyde of the formula (IIa) in which $R'_1$ and $R'_5$ are each hydrogen and $R_2$ and $R_4$ are each methoxy, and X is methyl, is converted to an aldehyde of the formula (Ia) in which $R_1$ and $R_5$ are each hydrogen and $R_2$ and $R_4$ are each methoxy.

20. The process according to claim 14, wherein an aldehyde of the formula (IIc)

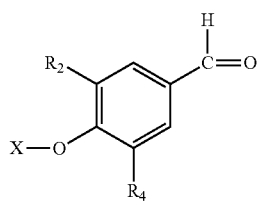

(IIc)

in which $R_2$ and $R_4$ are each independently hydrogen or $C_1$-$C_4$-alkoxy, and X is $C_1$-$C_4$-alkyl is converted to an aldehyde of the formula (Ic)

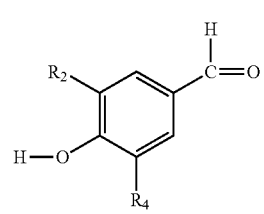

(Ic)

in which $R_2$ and $R_4$ are each as defined for formula (IIc).

21. The process according to claim 20, wherein $R_2$ and $R_4$ are each independently hydrogen, methoxy or ethoxy, and X is methyl.

22. The process according to claim 1, wherein the conversion is effected continuously.

* * * * *